United States Patent
Andree et al.

(12)

(10) Patent No.: US 6,184,183 B1
(45) Date of Patent: Feb. 6, 2001

(54) HETEROCYCLYLURACILS

(75) Inventors: Roland Andree; Mark Wilhelm Drewes, both of Langenfeld (DE); Markus Dollinger, Overland Park, KS (US)

(73) Assignee: Bayer Aktiengesellschaft, Leverkusen (DE)

(*) Notice: Under 35 U.S.C. 154(b), the term of this patent shall be extended for 0 days.

(21) Appl. No.: 09/319,753

(22) PCT Filed: Dec. 5, 1997

(86) PCT No.: PCT/EP97/06820

§ 371 Date: Jun. 10, 1999

§ 102(e) Date: Jun. 10, 1999

(87) PCT Pub. No.: WO98/27083

PCT Pub. Date: Jun. 25, 1998

(30) Foreign Application Priority Data

Dec. 17, 1996 (DE) .................................. 196 52 431

(51) Int. Cl.$^7$ ..................... C07D 401/04; C07D 403/04; A01N 43/54
(52) U.S. Cl. .................. 504/243; 544/212; 544/238; 544/310; 544/182
(58) Field of Search ................ 504/243; 544/212, 544/238, 310, 182

(56) References Cited

U.S. PATENT DOCUMENTS

| | | | |
|---|---|---|---|
| 3,920,653 | 11/1975 | Wenzelburger et al. | 260/256.4 C |
| 5,169,431 | 12/1992 | Enomoto et al. | 71/92 |
| 5,532,203 | 7/1996 | Fory et al. | 504/105 |
| 5,612,288 | 3/1997 | Fory et al. | 504/254 |
| 5,661,108 * | 8/1997 | Crawford et al. | 504/243 |
| 5,847,146 | 12/1998 | Schutze et al. | 546/309 |

FOREIGN PATENT DOCUMENTS

| | | |
|---|---|---|
| 22 07 549 * | 8/1973 | (DE) . |
| 3-287585 | 12/1991 | (JP) . |
| 5-202031 | 8/1993 | (JP) . |
| WO 89/10701 * | 11/1989 | (WO) . |
| 97/12284 | 4/1997 | (WO) . |

* cited by examiner

Primary Examiner—Mukund J. Shah
Assistant Examiner—Hong Liu
(74) Attorney, Agent, or Firm—Joseph C. Gil

(57) ABSTRACT

Novel heterocyclyluracils of the formula

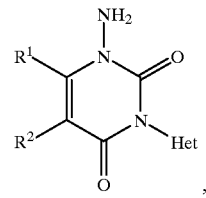

(I)

in which $R^1$, $R^2$ and Het are each as defined in the description, a process for preparing these substances and their use as herbicides.

4 Claims, No Drawings

HETEROCYCLYLURACILS

TECHNICAL FIELD OF THE INVENTION

The present invention relates to novel heterocyclyluracils, to a process for their preparation and to their use as herbicides.

BACKGROUND OF THE INVENTION

Numerous heterocyclyluracils having herbicidal and/or insecticidal properties are already known (cf. JP-A 91-287 585, JP-A 93 202 031, Chem. Abstr. 116, 235 650 and Chem. Abstr. 120, 107 048). Thus, for example, 1-(3-chloro-5-trifluoromethylpyridin-2-yl)-3,6-dihydro-2,6-dioxo-4-trifluoromethyl-1(2H)-pyrimidine can be used for controlling weeds. However, at low application rates, the activity of this substance is not always satisfactory.

DETAILED DESCRIPTION OF THE INVENTION

This invention, accordingly, provides novel heterocyclyluracils of the formula

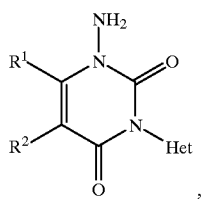

(I)

in which
R$^1$ represents formyl, hydroximinomethyl, cyano, carboxyl, alkoxycarbonyl, carbamoyl, thiocarbamoyl or represents optionally halogen-substituted C$_1$–C$_4$-alkyl,
R$^2$ represents hydrogen, cyano, halogen or represents opitionally halogen-substituted C$_1$–C$_4$-alkyl and
Het represents pyridinyl, pyrimidinyl, pyrazinyl, pyridazinyl, triazinyl, pyrazolyl, oxazolyl, isoxazolyl or thiazolyl, where these radicals are optionally mono- to trisubstituted by identical or different substituents selected from the group consisting of hydroxyl, mercapto, amino, cyano, nitro, carboxyl, carbamoyl, thiocarbamoyl, halogen, alkyl having 1 to 6 carbon atoms, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkylsulphonyl having 1 to 6 carbon atoms, halogenoalkylsulphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonyl-amino having 1 to 6 carbon atoms in the alkyl moiety and 1 to 6 carbon atoms in the alkylsulphonyl moiety, N-halogenoalkyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety and N-alkylsulphonyl-N-phenylcarbonyl-amino having 1 to 6 carbon atoms in the alkylsulphonyl moiety and being optionally mono- to trisubstituted by identical or different substituents selected from the group consisting of halogen, alkyl having 1 to 4 carbon atoms dialkylamino having 1 to 4 carbon atoms in each alkyl group and alkoxy having 1 to 4 carbon atoms.

Furthermore, it has been found that heterocyclyluracils of the formula (I) are obtained when
a) in a first step aminoalkenoic esters of the formula

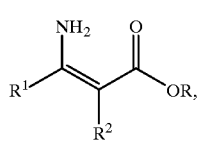

(II)

in which
R$^1$ and R$^2$ are each as defined above and
R represents alkyl, aryl or arylalkyl are either reacted
α) with heterocyclyl isocyanates of the formula

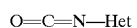 (III), in which
Het is as defined above,
or
β) with heterocyclyl carbamates of the formula

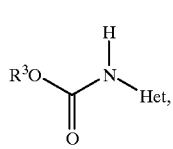

(IV)

in which

Het is as defined above and

R³ represents alkyl, aryl or arylalkyl, in each case if appropriate in the presence of an acid binder and if appropriate in the presence of a diluent, and b) in a second step the resulting heterocycluracils of the formula

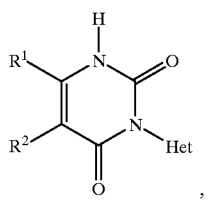

(V)

in which

R¹, R² and Het are each as defined above are reacted with 1-aminooxy-2,4-dinitrobenzene of the formula

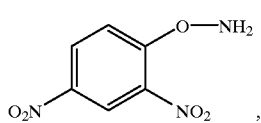

(VI)

if appropriate in the presence of an acid binder and if appropriate in the presence of a diluent.

Finally, it has been found that the novel heterocycluracils of the formula (I) have very good herbicidal properties.

Surprisingly, the heterocycluracils of the formula (I) according to the invention have considerably better herbicidal activity than the constitutionally most similar active compounds of the prior art which have the same direction of action.

In the present case, alkyl, alkoxy, alkylthio, alkylamino, dialkylamino, halogenoalkyl, halogenoalkoxy and halogenoalkylthio are in each case to be understood as straight-chain or branched radicals.

Unless stated otherwise, halogen in the present case represents fluorine, chlorine, bromine or iodine.

The formula (I) provides a general definition of the heterocycluracils according to the invention. Preference is given to compounds of the formula (I) in which R¹ represents formyl, hydroximinomethyl, cyano, carboxyl, alkoxycarbonyl having 1 to 4 carbon atoms in the alkoxy moiety, carbamoyl, thiocarbamoyl or represents alkyl having 1 to 3 carbon atoms which is optionally mono- to trisubstituted by identical or different substituents selected from the group consisting of fluorine and chlorine, R² represents hydrogen, cyano, fluorine, chlorine, bromine or represents alkyl having 1 to 3 carbon atoms which is optionally mono- to trisubstituted by identical or different substituents selected from the group consisting of fluorine and chlorine and Het represents pyridinyl, pyrimidinyl, pyrazinyl, pyridazinyl, triazinyl, pyrazolyl, oxazolyl, isoxazolyl or thiazolyl, where these radicals are optionally mono- to trisubstituted by identical or different substituents selected from the group consisting of hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 to 4 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 to 4 carbon atoms, alkoxyalkoxy having 1 to 4 carbon atoms in each alkoxy moiety, alkylthio having 1 to 4 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxycarbonyl having 1 to 3 fluorine and/or chlorine atoms and 1 to 4 carbon atoms in the halogenoalkoxy moiety, alkylamino having 1 to 4 carbon atoms, dialkylamino having 1 to 4 carbon atoms in each alkyl moiety, halogenoalkylamino having 1 to 3 halogen atoms and 1 to 4 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonylamino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoalkylcarbonyl group and having 1 to 3 fluorine and/or chlorine atoms and 1 to 4 carbon atoms in the halogenoalkylsulphonyl moiety and N-alkylsulphonyl-N-phenylcarbonylamino having 1 to 4 carbon atoms in the alkylsulphonyl moiety and being optionally mono- to trisubstituted by identical or different substituents selected from the group consisting of fluorine, chlorine, bromine, methyl, ethyl, n-propyl, i-propyl, n-butyl, i-butyl, s-butyl, t-butyl, dimethylamino, diethylamino, methoxy, ethoxy, n-propoxy and i-propoxy.

Particular preference is given to heterocycluracils of the formula (I), in which R¹ represents carboxyl, methoxycarbonyl, cyano, carbamoyl, thiocarbonyl or represents ethyl or methyl which is mono- to trisubstituted by identical or different substituents selected from the group consisting of fluorine and chlorine, R² represents hydrogen, fluorine, chlorine, bromine or methyl and Het represents pyridinyl, pyrimidinyl, pyrazinyl, pyridazinyl, triazinyl, pyrazolyl, oxazolyl, isoxazolyl or thiazolyl, where these radicals are optionally mono- to trisubstituted by identical or different substituents selected from the group consisting of hydroxyl, mercapto, amino, cyano, nitro, carboxyl, carbamoyl, thiocarbamoyl, fluorine, chlorine, bromine, iodine, alkyl having 1 to 4 carbon atoms, alkoxyalkyl having 1 or 2 carbon atoms in the alkyl moiety and 1 or 2 carbon atoms in the alkoxy moiety, alkoxy having 1 to 4 carbon atoms, halogenoalkoxy having 1 to 3 fluorine and/or chlorine atoms and 1 or 2 carbon atoms, alkoxyalkoxy having 1 or 2 carbon atoms in each alkoxy moiety, alkylthio having 1 or 2 carbon atoms, halogenoalkylthio having 1 to 3 fluorine and/or chlorine atoms and 1 to 4 carbon atoms, alkylsulphinyl having 1 to 4 carbon atoms, halogenoalkylsulphinyl having 1 to 3 fluorine and/or chlorine atoms and 1 to 4 carbon atoms, alkylsulphonyl having 1 to 4 carbon atoms, halogenoalkylsulphonyl having 1 to 3 fluorine and/or chlorine atoms and 1 to 4 carbon atoms, alkylcarbonyl having 1 to 4 carbon atoms in the alkyl moiety, halogenoalkylcarbonyl having 1 to 3 fluorine and/or chlorine atoms and 1 to 4 carbon atoms in the halogenoalkyl moiety, alkoxycarbonyl having 1 to 4 carbon atoms in the alkoxy moiety, halogenoalkoxy carbonyl having 1 to 3 fluorine and/or chlorine atoms and 1 to 4 carbon atoms in the halogenoalkoxy moiety, alkylamino having 1 to 3 carbon atoms, dialkylamino having 1 to 3 carbon atoms in each alkyl moiety, halogenoalkylamino having 1 to 3 fluorine and/or chlorine atoms and 1 to 3 carbon atoms, alkylaminocarbonyl having 1 to 4 carbon atoms in the alkyl moiety, dialkylaminocarbonyl having 1 to 4 carbon atoms in each alkyl moiety, alkylsulphonylamino having 1 to 4 carbon atoms, halogenoalkylsulphonylamino having 1 to 3 fluorine and/or chlorine atoms and 1 to 4 carbon atoms, N,N-bis-alkylsulphonylamino having 1 to 4 carbon atoms in each alkyl moiety, N,N-bis-halogenoalkylsulphonylamino having 1 to 3 fluorine and/or chlorine atoms and 1 to 4 carbon atoms in each halogenoalkyl moiety, N-alkyl-N-alkylsulphonyl-amino having 1 to 4 carbon atoms in the alkyl moiety and 1 to 4 carbon atoms in the alkylsulphonyl moiety, N-halogenoalkyl-N-halogenoalkylsulphonyl-amino having 1 to 3 fluorine and/or chlorine atoms and 1 to 4 carbon atoms in the halogenoalkyl moiety and having 1 to 3 fluorine and/or chlorine atoms and 1 to 4 carbon atoms in the halogenoalkylsulphonyl moiety, N-alkylcarbonyl-N-alkylsulphonyl-amino having 1 to 4 carbon atoms in the alkyl moiety of the alkylcarbonyl group and 1 to 4 carbon atoms in the alkylsulphonyl moiety, N-halogenoalkylcarbonyl-N-halogenoalkylsulphonyl-amino having 1 to 3 fluorine and/or chlorine atoms and 1 to 4 carbon atoms in the halogenoalkyl moiety of the halogenoaklylcarbonyl group and having 1 to 3 fluorine and/or chlorine atoms and 1 to 4 carbon atoms in the halogenoalkylsulphonyl moiety and N-alkylsulphonyl-N-phenylcarbonylamino having 1 to 4 carbon atoms in the alkylsulphonyl moiety and being optionally mono- to trisubstituted by identical or different substituents selected from the group consisting of fluorine, chlorine, bromine, methyl, ethyl, dimethylamino, diethylamino, methoxy and ethoxy.

Very particular preference is given to heterocyclyluracils of the formula (I), in which R¹ represents carboxyl, methoxycarbonyl, cyano, carbamoyl, thiocarbamoyl, methyl or trifluoromethyl, R² represents hydrogen and Het represents the heterocyclic radical of the following formulae:

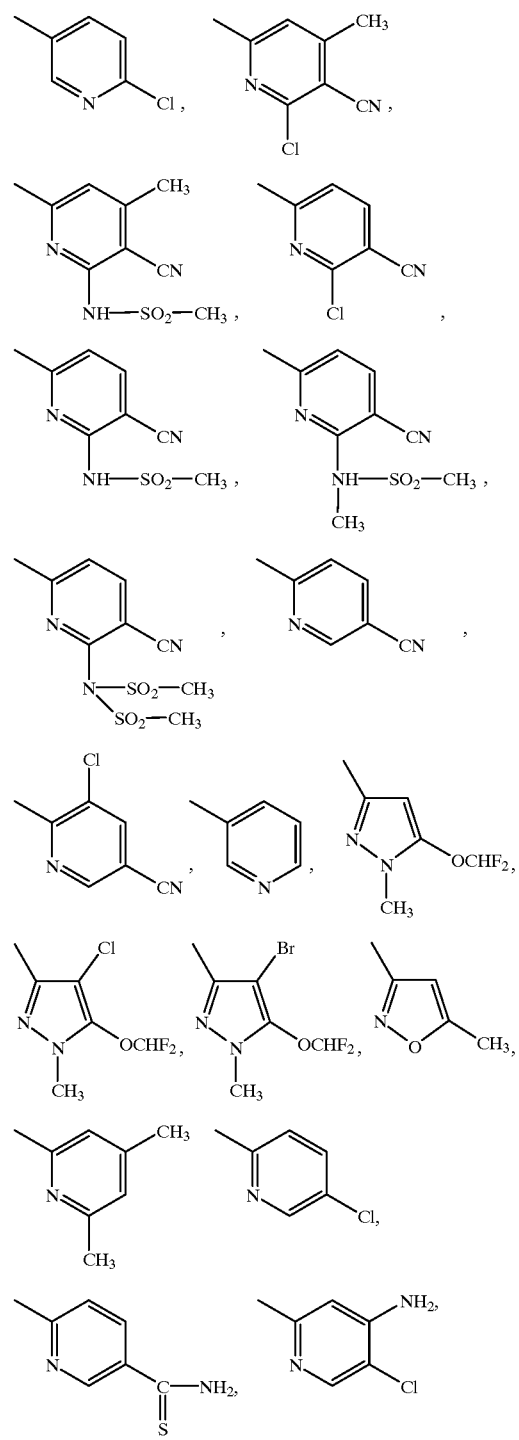

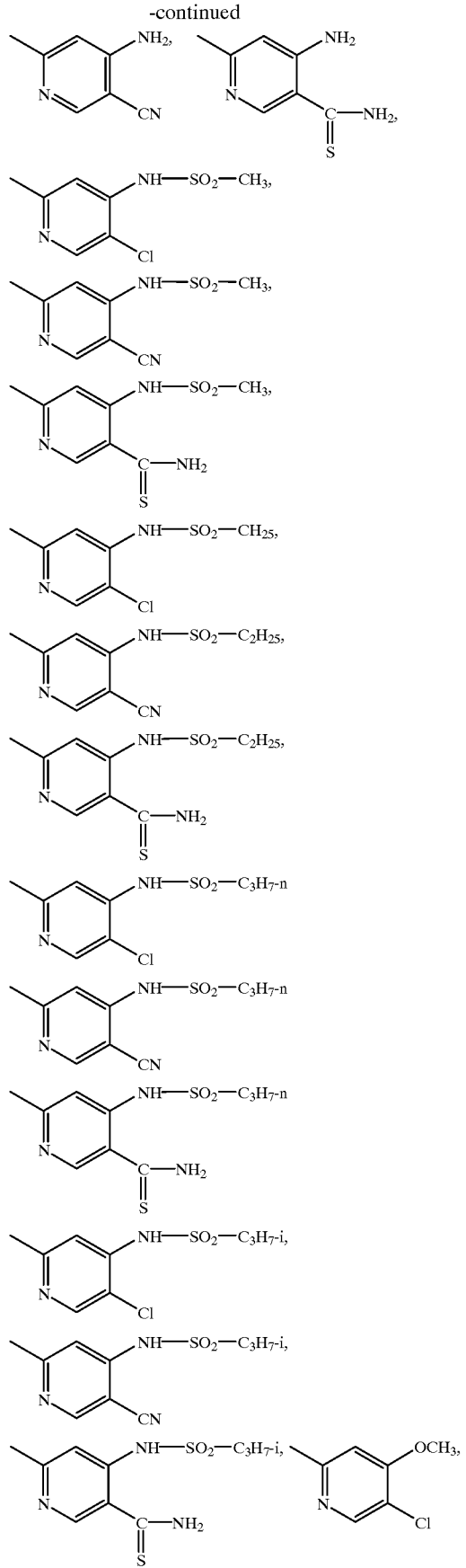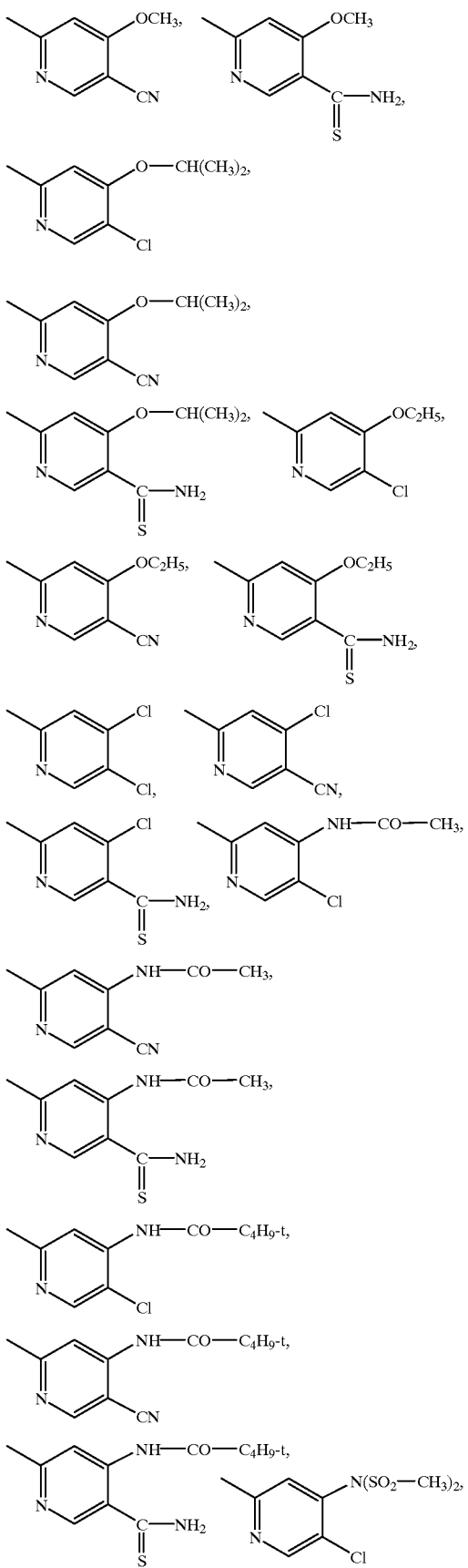

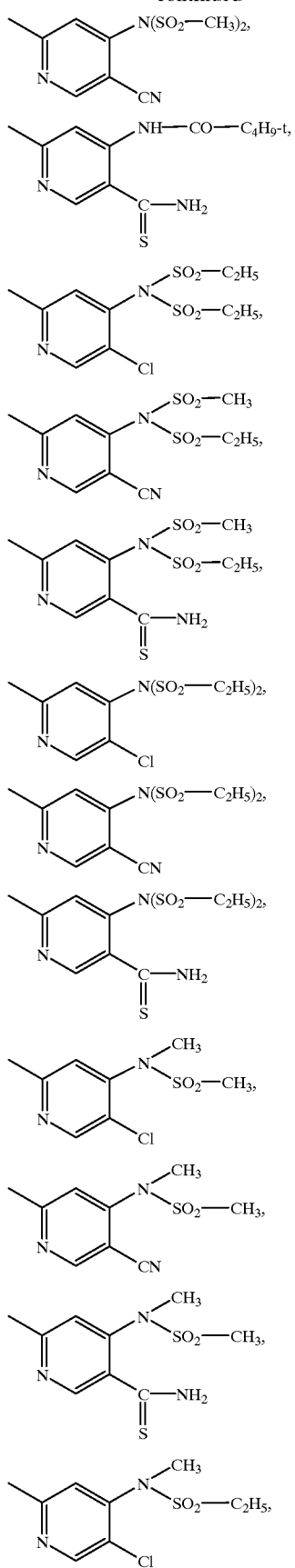
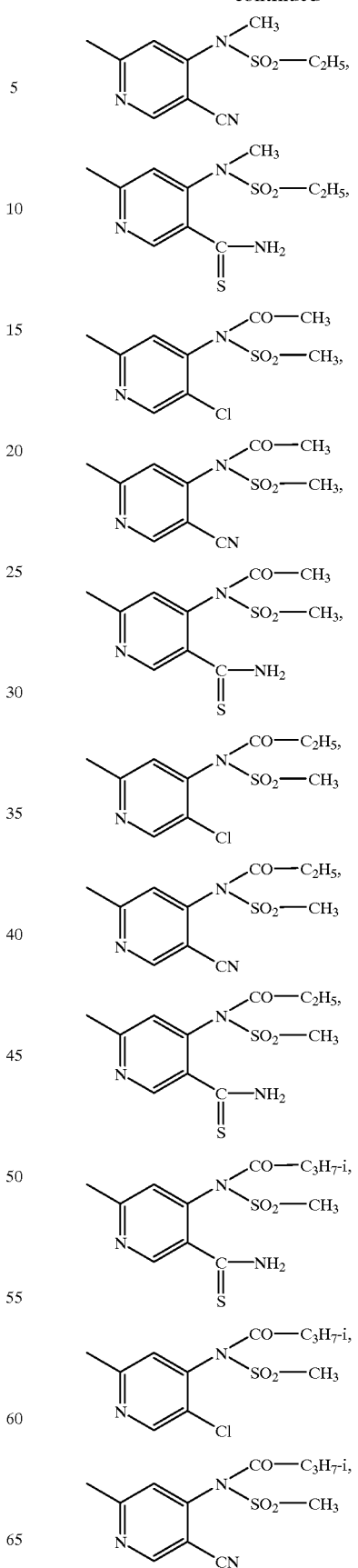

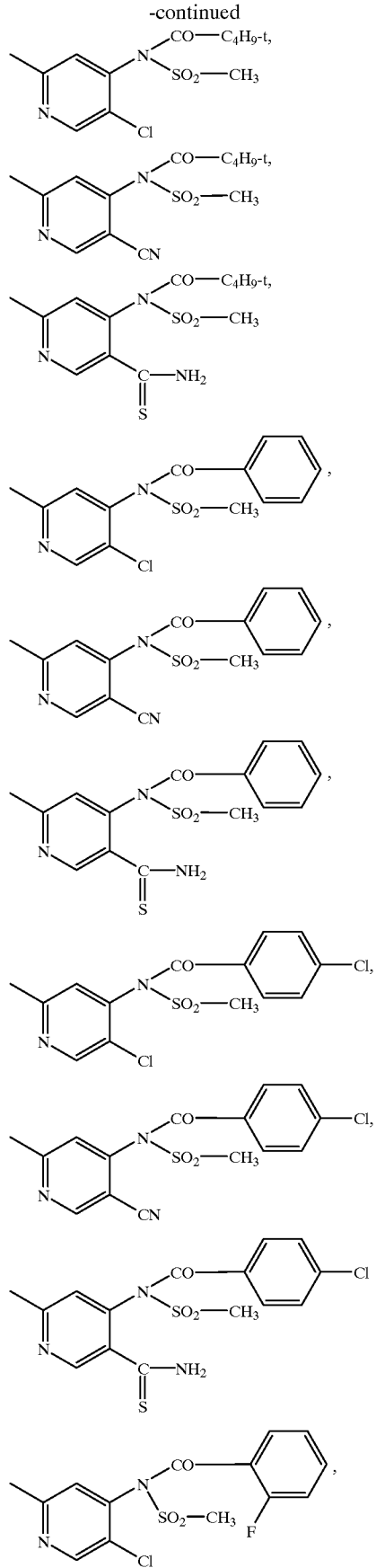
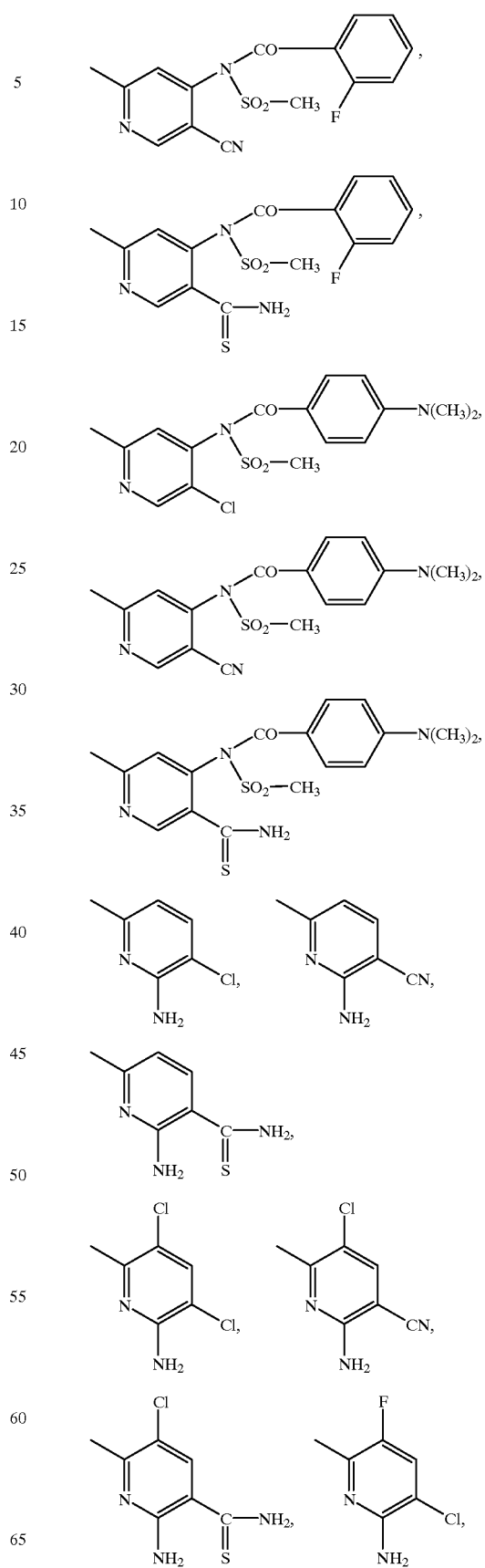

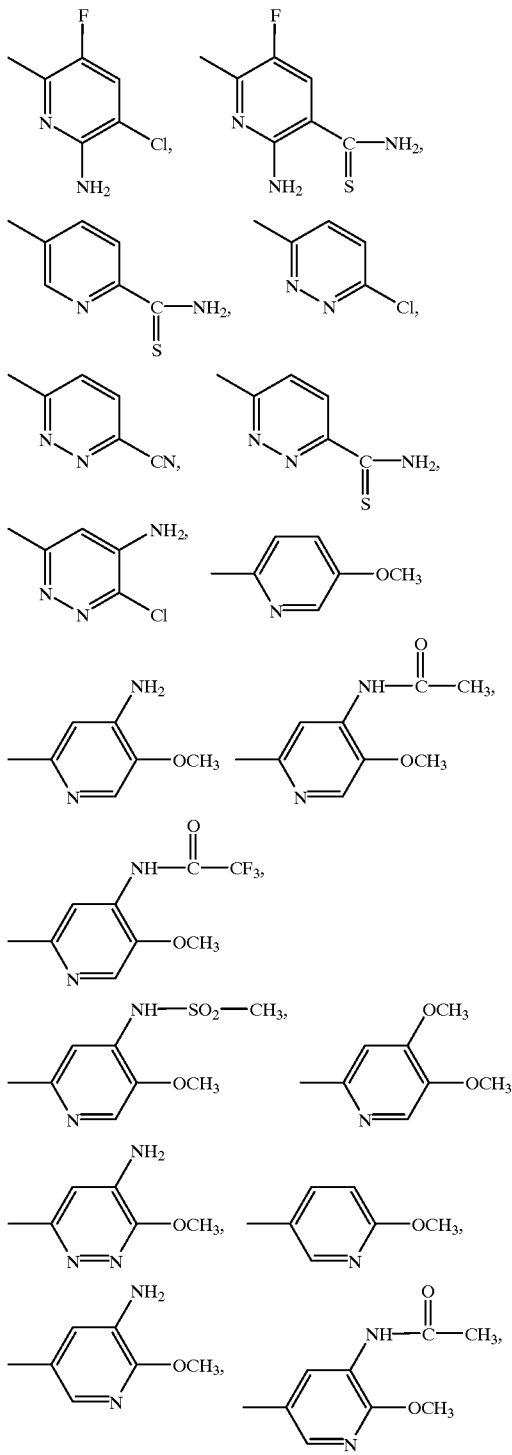

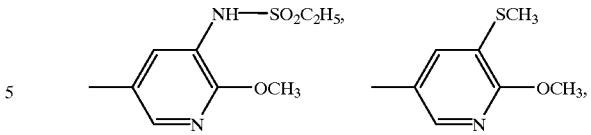

The abovementioned radical definitions apply both to the end products of the formula (I) and also, correspondingly, to the starting materials or intermediates required in each case for the preparation. These radical definitions can be combined with each other as desired, i.e. including combinations between the ranges given.

Using methyl 3-amino-crotonate and pyridin-3-yl isocyanate as starting materials and reacting the resulting 1-(pyridin)3-yl)-3,6-dihydro-2,6-dioxo-4-methyl-1(2H)-pyrimidine with 1-aminooxy-2,4-dinitro-benzene, the course of the process according to the invention can be illustrated by the following equation:

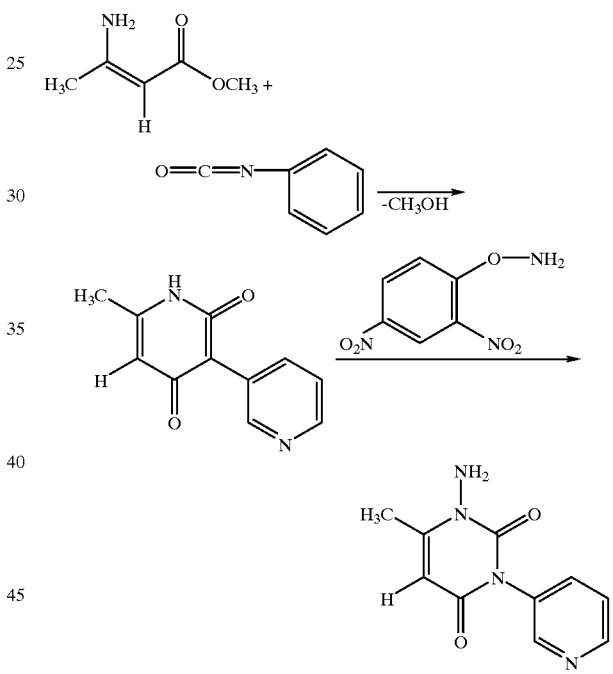

Using ethyl 3-amino-4,4,4-trifluorocrotonate and N-(2-chloro-3-cyano-4-methyl-pyridin-6-yl)-carbamate as starting materials and reacting the resulting 1-(2-chloro-3-cyano-4-methyl-pyridin-6-yl)-3,6-dihydro-2,6-dioxo-4-trifluoromethyl-1(2H)-pyrimidine with 1-aminooxy-2,4-dinitro-benzene, the course of the process according to the invention can be illustrated by the following equation:

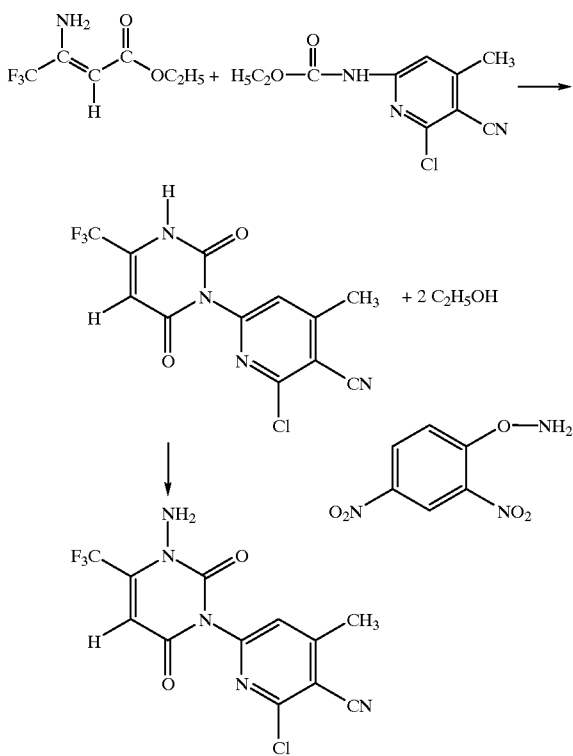

The formula (II) provides a general definition of the aminoalkenoic esters required as starting materials for carrying out the first step of the process according to the invention. In the formula (II), $R^1$ and $R^2$ each preferably or in particular have those meanings which have already been mentioned above, in connection with the description of the compounds of the formula (I) according to the invention, as being preferred or as being particularly preferred for $R^1$ and $R^2$. R preferably represents alkyl having 1 to 4 carbon atoms, phenyl and benzyl, particularly preferably represents methyl, ethyl, phenyl or benzyl.

The aminoalkenoic esters of the formula (II) are known or can be prepared by processes known per se (cf. J. Heterocycl. Chem. 9 (1972), 513–522).

The formula (III) provides a general definition of the heterocyclyl isocyanates required as reaction components for carrying out the first step, variant α, of the process according to the invention. In the formula (III), Het preferably or in particular has those meanings which have already been mentioned above, in connection with the description of the compounds of the formula (I) according to the invention, as being preferred or as being particularly preferred for Het.

The heterocyclyl isocyanates of the formula (III) are known or can be prepared by processes which are known in principle (cf. EP-A 0 555 770 and EP-A 0 600 836). Thus, heterocyclyl isocyanates of the formula (III) can be prepared by reacting heterocyclyl amines of the formula $$H_2N-Het \quad (VII),$$

in which

Het is as defined above with phosgene in the presence of the diluent, such as, for example, chlorobenzene, at temperatures between −20° C. and +150° C.

The heterocyclylamines of the formula (VII) are known or can be prepared by processes which are known in principle.

The formula (IV) provides a general definition of the heterocyclyl carbamates required as reaction components for carrying out the first step, variant β, of the process according to the invention. In the formula (IV), Het preferably or in particular has those meanings which have already been mentioned above, in connection with the description of the compounds of the formula (I) according to the invention, as being preferred or as being particularly preferred for Het. $R^3$ preferably represents $C_1$–$C_4$-alkyl, phenyl or benzyl, in particular represents methyl, ethyl or phenyl.

The heterocyclyl carbamates of the formula (IV) are known or can be prepared by processes which are known in principle (cf. EP-A 0 555 770 and EP-A 0 600 836). Thus, heterocyclyl carbamates of the formula (IV) are obtained when heterocyclylamines of the formula $$H_2N-Het \quad (VII),$$

in which

Het is as defined above are reacted with chlorocarbonyl compounds of the formula $$R^3O-CO-Cl \quad (VIII),$$

in which $R^3$ is as defined above, if appropriate in the presence of an acid acceptor such as, for example, pyridine, and if appropriate in the presence of a diluent, such as, for example, methylene chloride, at temperatures between −20° C. and +100° C.

The formula (V) provides a general definition of the heterocyclyluracils required as starting materials for carrying out the second step of the process according to the invention. The substances in question can be prepared by the first step of the process according to the invention.

The 1-aminooxy-2,4-dinitro-benzene of the formula (VI) which is required as a reaction component for carrying out the second step of the process according to the invention is also known (cf. EP-A 0 476 697).

Suitable acid acceptors for carrying out the first step of the process according to the invention both according to variant (α) and according to variant (β) are all customary inorganic and organic bases. Preference is given to using alkali metal or alkaline earth metal acetates, amides, carbonates, bicarbonates, hydrides, hydroxides or alkoxides, such as sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as trimethylamine, triethylamine, tripropylamine, tributylamine, ethyldiisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the first step of the process according to the invention according to variants (α)

or (β) are all customary inert organic solvents, and also water. Preference is given to using aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters such as methyl acetate or ethyl acetate, or sulphoxides, such as dimethyl sulphoxide.

When carrying out the first step of the process according to the invention, the reaction temperatures can be varied within a relatively wide range. Both variant (α) and variant (β) are generally carried out between 0° C. and 200° C., preferably between 10° C. and 150° C.

The first step of the process according to the invention according to variant (α) and (β) is generally carried out under atmospheric pressure. However, it is in each case also possible to operate under elevated or reduced pressure, for example between 0.1 and 10 bar.

When carrying out the first step of the process according to the invention, in the case of variant (α) an approximately equimolar amount of heterocyclyl isocyanate of the formula (III) and in the case of the variant (β) an approximately equimolar amount of heterocyclyl carbamate of the formula (IV) is employed per mole of aminoalkenoic ester of the formula (II). However, it is in each case also possible to employ a relatively large excess of one of the components. The reactions are generally carried out in a suitable diluent and in the presence of an acid binder. The reaction mixture is stirred at the required temperature as long as is necessary and then worked up by customary methods.

Suitable acid binders for carrying out the second step of the process according to the invention are all customary inorganic and organic bases. Preference is given to using those acid acceptors which have already been mentioned as being preferred in connection with the description of the first step of the process according to the invention.

Suitable diluents for carrying out the second step of the process according to the invention are all inert organic solvents which are customary for such reactions. Preference is given to using nitriles, such as acetonitrile and butyronitrile, ketones, such as acetone, and furthermore amides, such as diemethylformamide and N-methylpyrrolidone.

When carrying out the second step of the process according to the invention, the reaction temperatures can likewise be varied within a relatively wide range. The second step is generally carried out at temperatures between 0° C. and 80° C., preferably between 10° C. and 60° C.

The second step of the process according to the invention is likewise generally carried out under atmospheric pressure. However, it is also possible to operate under elevated or, if no volatile components participate in the reaction, under reduced pressure.

When carrying out the second step of the process according to the invention, generally an approximately equimolar amount of 1-aminooxy-2,4-dinitrobenzene of the formula (VI) is employed per mole of heterocyclyluracil of the formula (V). However, it is also possible to employ a relatively large excess of one of the components. Work-up is carried out by customary methods.

The active compounds according to the invention have very good herbicidal activity and can be used as defoliants, complete desiccants, haulm killers and, especially, as weed-killers. By weeds in the broadest sense, there are to be understood all plants which grow in locations where they are undesirable. Whether the substances according to the invention act as total or selective herbicides depends essentially on the amount used. The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual cultures.

The compounds of the formula (I) according to the invention are suitable in particular for selectively controlling monocotyledonous and dicotyledonous weeds in monocotyledonous crops, both pre-emergence and post-emergence. They are also tolerated well by important crop plants such as maize and wheat.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and also very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol, polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible. In some cases, synergism can also occur.

Possible components for the mixtures are the following herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

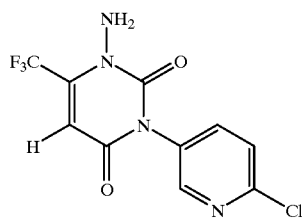

a) First Step

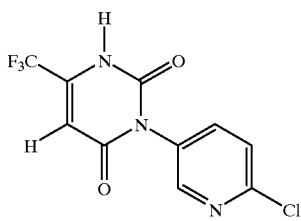
(V-1)

At 100° C. and under nitrogen, a mixture of 14.9 g (50 mmol) of ethyl 3-amino-4,4,4-trifluoro-crotonate, 13.8 g of potassium carbonate and 100 ml of N-methyl-pyrrolidone is stirred for one hour. 10.0 g (50 mmol) of O-ethyl N-(2-chloro-pyridin-5-yl)-carbamate are then added, and the reaction mixture is heated at approximately 130° C. on a water separator for four hours. Under nitrogen, the mixture is allowed to cool to room temperature and then poured into 1 litre of water and extracted three times with 100 ml of methylene chloride each time. The mixture is acidified with concentrated hydrochloric acid (to pH 3) and then left standing for one hour, and the crystalline product is isolated by filtration with suction.

This gives 10.6 g (75% of theory) of 1-(2-chloro-pyridin-5-yl)-3,6-dihydro-2,6-dioxo-4-trifluoromethyl-1(2H)-pyrimidine of melting point 158° C.

b) Second step

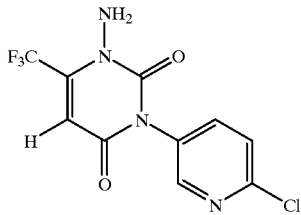

At room temperature, 3 g (13 mmol) of 1-aminooxy-2,4-dinitro-benzene are added a little at a time, with stirring and over a period of 60 minutes, to a mixture of 2.9 g (10 mmol) of 1-(2-chloro-pyridin-5-yl)-3,6-dihydro-2,6-dioxo-4-trifluoromethyl-1(2H)-pyrimidine, 0.9 g of sodium bicarbonate and 50 ml of N,N-dimethylformamide, the reaction mixture is stirred at room temperature for 48 hours. The mixture is then poured into a saturated aqueous sodium chloride solution and repeatedly extracted with ethyl acetate. The combined organic phases are washed with water, dried with sodium sulphate and filtered through silica gel. The filtrate is concentrated under water pump vacuum, the residue is digested with ethyl acetate and the crystalline product is isolated by filtration with suction.

This gives 1.7 g (55% of theory) of 3-amino-1-(2-chloro-pyridin-5-yl)-3,6-dihydro-2,6-dioxo-4-trifluoromethyl-1-(2H)-pyrimidine of melting point 235° C.

Preparation of the Starting Material of the Formula

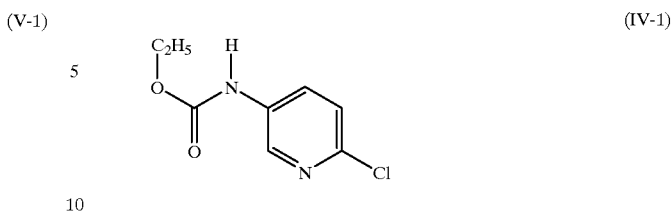
(IV-1)

With stirring, 11 g (0.1 mol) of ethyl chloroformate are added dropwise to a mixture of 12.8 g (0.1 mol) of 2-chloro-5-amino-pyridine, 15.8 g of pyridine and 200 ml of methylene chloride, and the reaction mixture is stirred at room temperature for three hours. The mixture is then washed with 1N hydrochloric acid, dried with sodium sulphate and filtered through silica gel. The solvent is carefully distilled off from the filtrate under water pump vacuum.

This gives 18.6 g (93% of theory) of O-ethyl N-(2-chloro-pyridin-5-yl)-carbamate as a crystalline product of melting point 110° C.

The compounds of the formula (I) listed in the examples below are likewise prepared by the methods given above.

Example 2

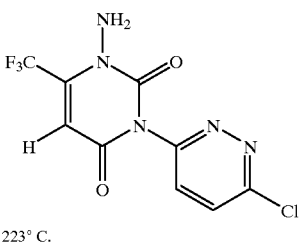

m.p. = 223° C.

Example 3

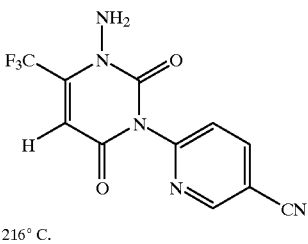

m.p. > 216° C.

Example 4

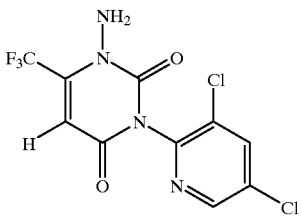

m.p. > 193° C.

Example 5

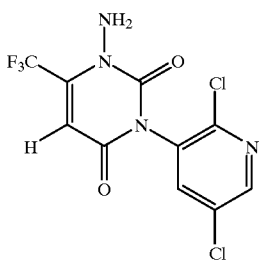

m.p. 190° C.

Example 6

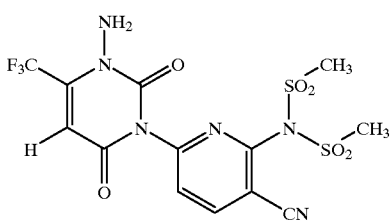

m.p. 270° C.

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The figures denote:

0%=no effect (like untreated control)

100%=total destruction

In this test, the compounds of Preparation Examples 1 and 2 exhibit strong activity against weeds, and they are in some instances tolerated well by crop plants, such as maize and soya bean.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with a preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The figures denote:

0%=no effect (like untreated control)

100%=total destruction

In this test, the compounds of Preparation Examples 1 and 2 exhibit strong activity against weeds, and in some instances they are tolerated well by crop plants, such as wheat.

What is claimed is:

1. A heterocyclyluracil of the formula:

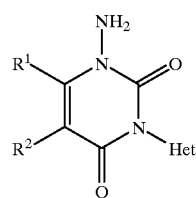

(I)

wherein $R^1$ represents formyl, hydroximinomethyl, alkoxycarbonyl having 1 to 4 carbon atoms in the alkoxy moiety, carbamoyl, thiocarbamoyl or $CF_3$ $R^2$ represents hydrogen, cyano, halogen or unsubstituted or halogen-substituted $C_1$–$C_4$-alkyl and Het represents pyridinyl, pyrimidinyl, pyrazinyl, pyridazinyl, triazinyl, pyrazolyl, oxazolyl, isoxazolyl or thiazolyl, where these radicals are unsubstituted or mono- to trisubstituted by identical or different substituents selected from the group consisting of hydroxyl, mercapto, amino, cyano, nitro, carboxyl, carbamoyl, thiocarbarnoyl, halogen, alkyl having 1 to 6 carbon atoms, alkoxyalkyl having 1 to 4 carbon atoms in the alkoxy moiety and 1 to 6 carbon atoms in the alkyl moiety, alkoxy having 1 to 6 carbon atoms, halogenoalkoxy having 1 to 6 carbon atoms and 1 to 5 halogen atoms, alkoxyalkoxy having 1 to 6 carbon atoms in each alkoxy moiety, alkylthio having 1 to 6 carbon atoms, halogenoalkylthio having 1 to 6 carbon atoms and 1 to 5 halogen atoms, alkylsulphinyl having 1 to 6 carbon atoms, halogenoalkylsulphinyl having 1 to 6 carbon atoms and 1 to 5 halogen atoms, alkysulphonyl having 1 to 6 carbon atoms, halogenoalkylsuphonyl having 1 to 6 carbon atoms and 1 to 5 halogen atoms, alkylcarbonyl having 1 to 6 carbon atoms in the alkyl moiety, halogenoalkylcarbonyl having 1 to 5 halogen atoms and 1 to 6 carbon atoms in the halogenoalkyl moiety, alkoxycarbonyl having 1 to 6 carbon atoms in the alkoxy moiety, halogenoalkoxycarbonyl having 1 to 5 halogen atoms and 1 to 6 carbon atoms in the halogenoalkoxy moiety, alkylamino having 1 to 6 carbon atoms, dialkylamino having 1 to 6 carbon atoms in each alkyl moiety, halogenoalkylamino having 1 to 5 halogen atoms and 1 to 6 carbon atoms, alkylaminocarbonyl having 1 to 6 carbon atoms in the alkyl moiety, dialkylaminocarbonyl having 1 to 6 carbon atoms in each alkyl moiety, alkylsulphonylamino having 1 to 6 carbon atoms in the alkyl moiety, halogenoalkylsulphonylamino having 1 to 5 halogen atoms and 1 to 6 carbon atoms in the halogenoalkyl moiety, N,N-bis-alkylsulphonylamino having 1 to 6 carbon atoms in each alkyl moiety, N,N-bis-halogenoalkylsulphonyl-amino having 1 to 5 halogen atoms and 1 to 6 carbon atoms in each halogenoalkyl moiety, N-alkyl-N-alkylsulphonylamino having 1 to 6 carbon atoms in the alkyl moiety and 1 to 6 carbon atoms in the alkylsulphonyl moiety, N-halogenoalkyl-N-halogeno-alkylsulphonyl-amino having 1 to 5 halogen atoms and 1 to 6 carbon atoms in the halogenoalkyl moiety and 1 to 5 halogen atoms and 1 to 6 carbon atoms in the halogenoalkylsulphonyl moiety, N-alkylcarbonyl-N-alkylsulphonyl-amino having 1 to 6 carbon atoms in the alkyl moiety of the alkylcarbonyl group and 1 to 6 carbon atoms in the alkylsulphonyl moiety, N-halogenoalkylcarbonyl-N-halogenoalkylsulphonyl-amino having 1 to 5 halogen atoms and 1 to 6 carbon atoms in the halogenoalkyl moiety and 1 to 5 halogen atoms and 1 to 6 carbon atoms in the halogeno-alkylsulphonyl moiety and N-alkylsulphonyl-N-phenyl-carbonylamino having 1 to 6 carbon atoms in the alkylsulphonyl moiety and being unsubstituted or mono- to trisubstituted by identical or different substituents selected from the group consisting of halogen, alkyl having 1 to 4 carbon atoms, dialkylamino having 1 to 4 carbon atoms in each alkyl group and alkoxy having 1 to 4 carbon atoms.

2. A herbicidal composition comprising at least one heterocyclyluracil of formula (I) of claim 1 and one or more extenders and/or surfactants.

3. A method for controlling weeds, comprising the step of applying a heterocyclyluracil of formula (I) of claim 1 to the weeds and/or their habitat.

4. A process for preparing a herbicidal composition, comprising the step of mixing a heterocyclyluracil of formula (I) according to claim 1 with extenders and/or surfactants.

\* \* \* \* \*